United States Patent
Underhill et al.

[11] Patent Number: 6,050,150
[45] Date of Patent: Apr. 18, 2000

[54] DIFFUSIVE SAMPLER

[76] Inventors: Dwight W Underhill, 119 Rusty Barn Rd., Columbia, S.C. 29212; Charles E Feigley, 2538 Wheat St., Columbia, S.C. 29205

[21] Appl. No.: 08/923,959

[22] Filed: Sep. 5, 1997

[51] Int. Cl.[7] .................................................. G01N 1/00
[52] U.S. Cl. .......................... 73/863; 210/690; 210/694; 436/178
[58] Field of Search ................ 73/23.35, 23.41, 73/23.42, 863, 863.21; 210/694; 422/69, 88, 83; 436/178

[56] References Cited

U.S. PATENT DOCUMENTS

| | | |
|---|---|---|
| 3,950,980 | 4/1976 | Braun et al. . |
| 3,992,153 | 11/1976 | Ferber et al. . |
| 4,040,805 | 8/1977 | Nelms et al. . |
| 4,046,014 | 9/1977 | Boehringer et al. . |
| 4,327,575 | 5/1982 | Locker . |
| 4,328,181 | 5/1982 | Anders et al. . |
| 4,350,037 | 9/1982 | Higham . |
| 4,419,326 | 12/1983 | Santini . |
| 4,445,364 | 5/1984 | Stiieff et al. . |
| 4,692,309 | 9/1987 | Pannwitz . |
| 4,701,306 | 10/1987 | Lawrence et al. . |
| 4,913,882 | 4/1990 | May et al. . |
| 5,110,558 | 5/1992 | Romer ................................. 73/863.21 |
| 5,168,068 | 12/1992 | Yanagisawa et al. . |
| 5,173,264 | 12/1992 | Zaromb et al. . |
| 5,482,677 | 1/1996 | Yao et al. . |

*Primary Examiner*—Hezron Williams
*Assistant Examiner*—Thuy Vinh Tran
*Attorney, Agent, or Firm*—Michael A. Mann; Nexsen Pruet Jacobs & Pollard LLP

[57] ABSTRACT

A diffusive sampler comprises a housing with an opening and containing a sorbent, preferably having a barrier between the sorbent and the opening to prevent convection currents but still allowing the exchange of the analyte and the sorbate(s) by diffusion, and at least one sorbate carried by the sorbent. The sorbates will be desorbed when the sampler is exposed to the fluid to provide a check on the apparent duration of the exposure and a correction to the calculation of analyte concentration in the fluid that results from desorption and reverse diffusion. The barrier may be either a fluid-permeable matrix or a fluid gap with a thin, fluid-permeable membrane for blocking convection currents but otherwise admitting fluid and analyte.

20 Claims, 1 Drawing Sheet

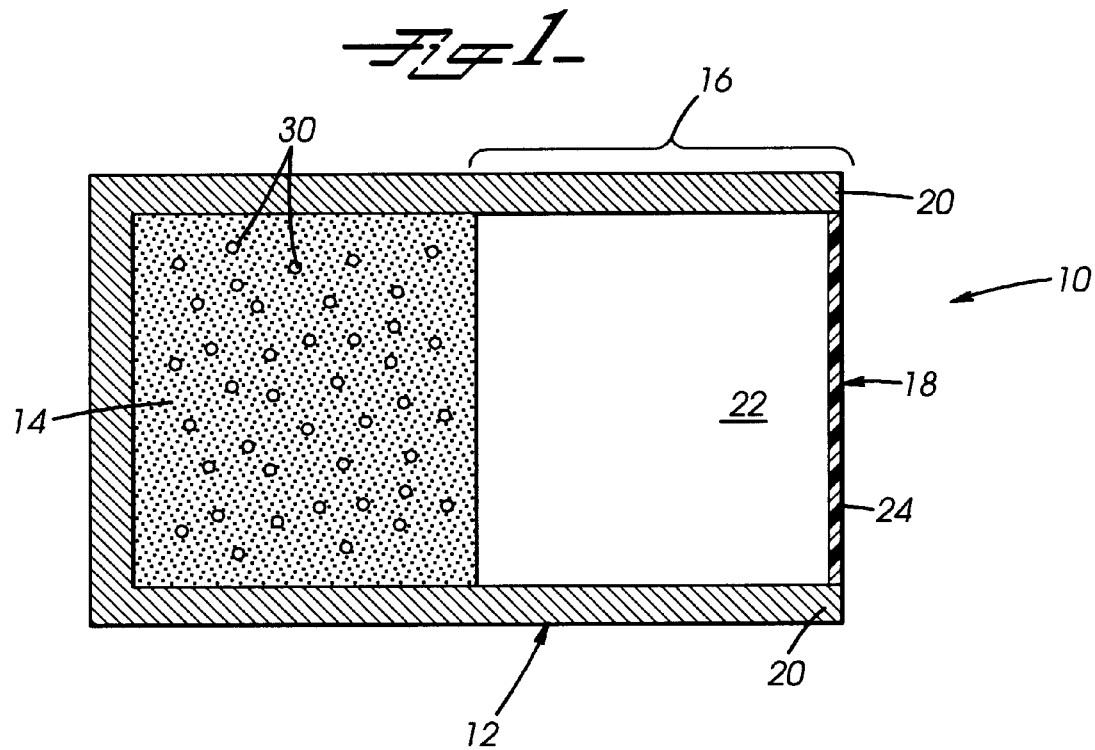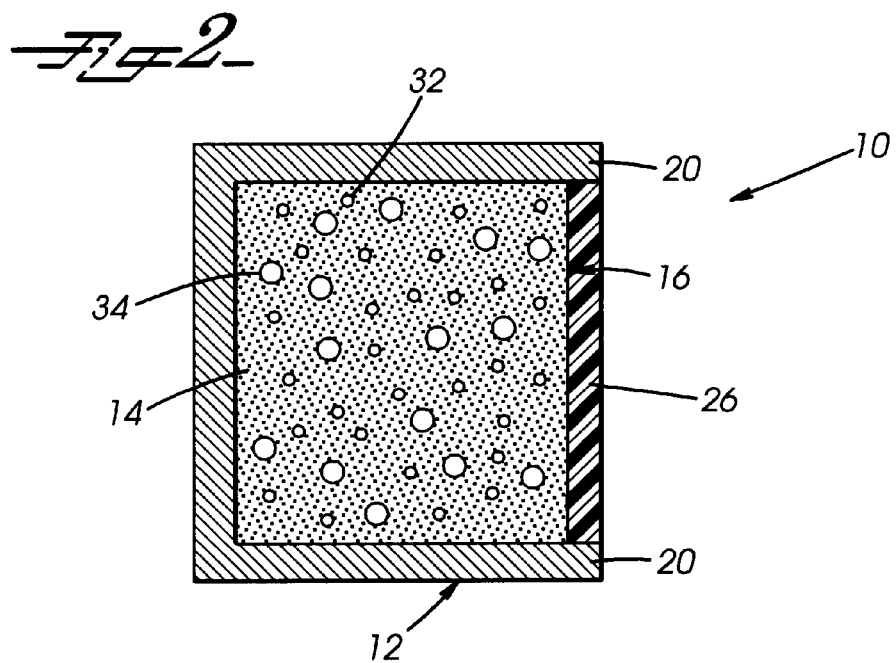

DIFFUSIVE SAMPLER

1. FIELD OF THE INVENTION

The present invention relates to air and water samplers, and in particular, a diffusive sampler capable of providing more accurate information about the concentration of an analyte.

2. BACKGROUND OF THE INVENTION

A diffusive sampler is in concept a simple device for determining the presence of a chemical substance—the "analyte"—in a fluid by exposing the device to the fluid so that analyte carried by the fluid can be sorbed by an sorbent in the device, thereby being bound in the sampler. These devices are also called "air samplers" or "gas samplers" because of their use in sampling airborne, gaseous chemicals.

Diffusive samplers are commonly used in the workplace for monitoring workers' exposures to toxic gases and vapors. They can be inexpensive to manufacture, small and convenient to wear, and are often simple to analyze.

The use of diffusive sampling to determine the concentration of toxic chemicals in the workplace goes back many decades. For example, in *Methods of Air Analysis* published by Charles Griffen and Co. in 1912, J. S. Haldane reported that "The presence of sulphuretted hydrogen [in current chemical terminology, hydrogen sulfide] can easily be recognized chemically by the blackening of a strip of paper which has been dipped into acetate of lead solution. Any air in which this blackening occurs within a minute should be regarded as very dangerous." He also reported that: (1) nitrous fumes could be sensed using a strip of paper moistened with a solution of starch and potassium iodide, which solution turns blue in the presence of the nitrous fumes, and (2) phosphine blackens paper dipped in silver nitrate.

Around 1952, the Central Intelligence Agency used a type of diffusive sampler it called a "sneaky" which was a chemically treated handerchief. After exposure to the air for a minute, the handkerchief would pick up factory fumes that could later be analyzed and identified. However well-suited sneakies were for determining the presence of unknown substances, their ability to yield information about concentrations of those substances was very limited.

In environmental monitoring, diffusive samplers are also well known. For example, it was once common to measure environmental sulfur dioxide by coating a tube or plate with lead peroxide and exposing the plate to the environment for several weeks to several months. If sulphur dioxide were present in that environment, it would react with the sulphur to form lead sulfate, the presence and concentration of which could be detected and quantified by analysis. However, after more accurate analytical techniques were developed, it was clear that there was little correlation between these newer techniques and the diffusive sampler for sulphur dioxide.

Although there were a number of attempts to increase the accuracy of these diffusive samplers for sulphur dioxide, none was successful because the accuracy of the sampler depended on a complete understanding of the interaction of the analyte and the surface of the sampler, a fact not fully appreciated at the time. Diffusion into a material depends intimately on the nature of the surface of that material. Furthermore, reproducing the nature of a lead oxide surface requires considerable technical capability.

Although diffusive samplers have a number of advantages, the inability to accurately quantify the concentration of the analyte had limited their use and effectiveness. Clearly important were the variations in air flow where the sampler was used. Mass transfer through the laminar flow of air adjacent to the sampler surface depends on the thickness of the laminar layer, which in turn depends on the turbulent flow of air beyond the laminar layer.

Another source of errors is exposure to the air after the sampling period. Because analytes may also desorb when the sampler is exposed to the air after the sampling period, the diffusive sampler should be packaged or sealed in a vapor-proof package as soon as the sampling period ends.

There have been some attempts to solve these problems. E. D. Palmes and G. D. Gunnison in "Personal Monitoring Device for Gaseous Contaminants," published in the *American Industrial Hygiene Association Journal*, Vol. 32, pages 78–81 (1973), advanced the art in their diffusive sampler for nitrogen dioxide. They found that sampling accuracy can be improved by incorporating an internal diffusive mass transfer resistance (which can be maintained constant) which is greater than, and therefore suppresses the effects of, the variable external diffusive mass transfer resistance. For this purpose, their device (often called a "Palmes'tube") contained a quiescent air gap in front of the sampling substrate to limit the uptake rate to:

$$W=DACt/L,$$

where "W" is the uptake in micrograms, "D" is the diffusion coefficient for the analyte in air in square centimeters/second, "A" is the exposed sampling surface, "C" is the average airborne concentration of the analyte in micrograms per milliliter, "t" is the sampling period in seconds, and "L" is the length of the air gap in centimeters. After exposure and analysis, all factors except for the concentration "C" are known, and therefore "C" can be determined from the known factors using this equation. It is clear that the improvements of Palmes and Gunnison included both the use of the gap that made uptake of the analyte proportional to "t", the duration of exposure, and the use of a layer of known material—air, in particular—wherein the diffusion coefficients of many important compounds are already well known or easily measured.

Accuracy can be and also has been improved by impregnating the sampler with two sorbents having different sorption capacities, with the sorbent having the lower sorption capacity placed on the exterior surface. This arrangement is more effective when used in diffusive samplers intended to sample a very wide variety of contaminants having different molecular weights. Higher molecular weight contaminants are retained on the exposed layer, and the lower molecular weight contaminants penetrate to the interior layer. In the absence of this arrangement, one would have to select a sorbent that either (because of its low capacity) did not retain low molecular weight compounds, or (because of its high capacity) would not release the high molecular weight compounds for further analyses.

Locker, in U.S. Pat. No. 4,327,575, describes the use of two sorbent layers wherein the outer layer is used to remove undesirable components of the atmosphere before the analyte of interest reaches the inner layer.

Related diffusive devices are designed to emit analyte at a constant rate. They rely on Fick's first law of diffusion, known since the nineteenth century, which states that if the concentration difference across a membrane is held constant, then the steady state diffusion of analyte across the membrane will also be constrant. Devices incorporating this basic principle include:

1. Permeation tubes, in which (usually) a liquid aliquot of the analyte is held in a polytetrafluoroethylene tube, through which it diffuses very slowly (See page 130 of *The Industrial Environment—Its Evaluation and Control*, U.S. Department of Health, education and Welfare. 1993. Stock Number 017-001-0396-4). To maintain a constant emission rate, the tube is generally placed in an oven where the temperature can be carefully controlled.
2. Diffusion tubes, in which (usually) a liquid aliquot is placed in a glass bulb connected to a long necked stem. The loss of analyte is controlled by the vapor pressure of the analyte, the diffusion coefficient of its vapor in the ambient atmosphere, and the geometry of the long necked stem, An excellent description of this procedure is given by Altshuller and Cohen in *Application of Diffusion Cells to the Production of Known Concentrations of Hydrocarbons*, Analytical Chemistry 32:802 (1960).
3. Saturated beds of adsorbent (see U.S Pat. No. 4,445,364, Stieff et al.) that constantly lose analyte, thereby introducing a steady flow of analyte into an air stream.

None of these devices was designed for, or would be expected to be useful for, the sampling of analytes from the atmosphere.

This review of these diffusion-based devices shows that there remains a need for an improved diffusive sampler that can be used to determine more accurately the presence and the concentration of the analyte.

SUMMARY OF THE INVENTION

According to its preferred embodiments and briefly stated, the present diffusive sampler comprises a housing containing a sorbent, a barrier and at least one sorbate. The sorbent is impregnated with the sorbates that desorb from the sorbent during exposure. The amounts of the sorbates remaining after a period of exposure, and the ratios of sorbates if two or more are used, provides means for correcting the calculation of the concentration of analyte based on the quantity of it retained by the sorbent.

Prior to exposure, the sorbent contains one or more sorbates that will desorb during exposure. If two or more are used, it is helpful if their desorption characteristics are sufficiently different so that the ratio of the amounts remaining after a period of exposure provides information about the duration of the exposure and yields a correction factor for loss of analyte from the sorbent as a result of reverse diffusion and desorption.

If one sorbate is used, the absolute amount of it remaining after exposure provides that information.

The use of one or more sorbates is an important feature of the present invention. Being able to detect gross errors in apparent exposure time and to correct for desorption and reverse diffusion of the analyte in the calculation of the actual concentration of the analyte during the exposure period, make it possible to use diffusive samplers according to the present invention for especially volatile chemicals and for very long-term diffusive sampling, where effectively accurate diffusive sampling has been unavailable.

In the present invention it is only necessary to have known amounts of sorbates or known ratios of sorbates placed on the sorbent. It is not necessary to saturate the sorbent with the sorbate(s). Saturating the sorbent would have the undesirable effect of reducing the uptake of analyte. As will be described below, achieving a constant emission rate of sorbate is generally not desirable because variations in the loss of sorbate(s) can be used to obtain an improved estimate of the ambient concentration of analyte.

Other features and their advantages will be apparent to those skilled in the art of diffusive samplers from a careful reading of the Detailed Description of Preferred Embodiments accompanied by the following drawings.

BRIEF DESCRIPTION OF THE DRAWINGS

In the drawings,

FIG. 1 is a schematic view of a diffusive sampler according to a preferred embodiment of the present invention; and FIG. 2 is a schematic view of an alternative diffusive sampler according to a preferred embodiment of the present invention.

DETAILED DESCRIPTION OF PREFERRED EMBODIMENTS

The present invention is a diffusive sampler. Referring now to the figures, both the embodiments of sampler 10 have a housing 12, a sorbent 14 containing at least one sorbate, and a barrier 16 to limit the diffusion of analyte.

In the first embodiment, illustrated in FIG. 1, barrier 16 includes an air gap 22 and a membrane 24 carried by walls 20 of housing 12. In FIG. 1, membrane 24 is preferably a thin sheet of cellulosic filter material or plastic that is sorbate- and analyte-permeable. Membrane 24 reduces the possibility of convection currents transporting analyte into sampler 10. In the second embodiment, as illustrated in FIG. 2, barrier 16 is a matrix 26 that serves the same purposes as membrane 24 and air gap 22 in FIG. 1.

Matrix 26 is a volume of plastic or aerogel or xerogel that is analyte- and sorbate-permeable and that serves the same purpose as the membrane and air gap. By avoiding convection currents, the diffusive flow into sorbent 14 is controlled, and the rate of mass transfer across it is more uniform. Thus the accuracy of the sampler is increased.

Housing 12 is preferably made of a material that is impervious to analyte and the fluid, such as a metal.

Sorbent 14 is selected to sorb the analyte. Selecting a sorbent is a routine task, once the identity of the analyte of interest is known, and well within the capability of those of ordinary skill in the art of diffusive samplers. Activated charcoal, for example, is a common sorbent for many chemicals, including many organic compounds.

During manufacture of sampler 10, a sorbate 30 is added to sorbent 14. Sorbate 30 is selected to be capable of being desorbed by sorbent 14 during exposure. During sampling, when sorbent 14 is exposed and at any other time sampler 10 is exposed, the loss of sorbate 30 from sampler 10 may occur.

If the loss of the sorbate 30 is abnormally low, so low that sampler 10 could not have been left exposed for the full sampling period, then sampler 10 has not been used properly. For example, if sampler 10 were sent to a laboratory for analysis after exposure to what was to have been an eight-hour workday but in reality was a fifteen-minute short term exposure level, the abnormally high level of sorbate 30 remaining in substrate 14 would indicate that the actual exposure duration was too short for an eight-hour day.

On the other hand, if the loss of sorbate 30 were abnormally high, the reverse might be true: an exposure for what should have been a fifteen-minute short term exposure level was in reality for an eight-hour workday. This condition could also be the result of a failure to properly seal sampler 10 between the end of the sampling period and the time of analysis in the laboratory.

If, however, the quantity of sorbate 30 is within the normal range, then the quantity of sorbate 30 remaining in sorbent 14 can be used to correct the observed uptake of analyte by sorbent 14 for the effect of the normal variations in the mass transfer resistance across the sampler. The loss of sorbate 30 from sampler 10 is affected by the changes in the external mass transfer resistance just as (or nearly so, because of differences in the Schmidt numbers of analyte and sorbate 30) the rate of uptake is affected by the boundary layer of fluid at barrier 16. The thin boundary layer observed at high fluid velocities would be conducive both to a higher-than-average uptake of analyte and a higher-than-average loss of sorbate 30. Because the initial concentration of sorbate is known, the appropriate correction factor may be found empirically, using a series of diffusive samplers such as sampler 10 exposed in a chamber at various air velocities, or calculated using the numerical procedure developed by Adley and Underhill in "Fundamental Factors in the Performance of Diffusive Samplers," *Analytical Chemistry*, Vol. 61, pages 917–922(1989), incorporated herein by reference, to describe mass transfer in diffusive samplers and the equation of Tompkins and Goldsmith for calculating mass transfer rates across laminar layers, namely:

$$k = 1.45 \left[\frac{D}{L}\right] Re_L^{0.4} Sc^{1/3},$$

where "k" is the convection mass transfer coefficient across the laminar film in centimeters per second; "L" is the length in centimeters across the diffusive sampler in the direction of air flow; "D" is the diffusion coefficient of the analyte in the fluid in square centimeters per second; "$Re_L$" is the dimensionless length Reynolds number; and "Sc" is the dimensionless Schmidt number.

Sorbate 30 is preferably chosen from compounds having the following properties: (1) a sufficiently high vapor pressure such that a significant desorption will occur if the sampler is allowed to desorb after the sampling period; (2) easily detected so that only trace levels of the second adsorbate need be placed onto the sorbent; (3) not commonly found in the sampled area so that uptake of the second sorbate from the atmosphere will not be a confounding factor; (4) chemically stable; (5) available; and (6) low toxicity. Preferably, sorbate 30 is one of the halogenated anesthetic agents, such as halothane. The high vapor pressure of halothane (permitting significant desorption by reverse diffusion), its electronegative halogen structure (permitting the detection of very low concentrations by electron capture gas chromatography), its general absence from all workplaces and other sampling areas (other than operating rooms), and its stability, all recommend this choice of compound over a number of other possible choices that would also satisfactorily meet the aforementioned requirements.

A second procedure, illustrated in FIG. 2, is to impregnate sorbent 14 before its use with two sorbents having significantly different adsorption coefficients. A first sorbate 32 would have the same characteristics as adsorbate 26; a second sorbate 34 will be selected to have a negligible rate of desorption and reverse diffusion from substrate 14. During exposure, the ratio of the first to the second sorbate will decrease in accordance with the time allowed. The ratio can indicate, for example, whether sampler 10 has been put in a situation where such a significant loss of analyte may have occurred that the sample is invalid. This ratio can also be used to determine a correction factor for the loss of analyte by desorption and reverse diffusion and thus determine the effect of the fluid boundary layer on the sampling rate.

An advantage of this second procedure is that it is necessary only to know the ratio of the two sorbates, 32, 34 and not either one's absolute amounts. The second sorbate 34 is preferably p-fluorobromobenzene, a substance used as an internal standard gas in chromatography but which is not a common atmospheric contaminant.

The following situation and examples illustrate the present invention.

XYZ Corporation uses very large quantities of solvents in manufacturing consumer products for wholesale distribution. These solvents evaporate readily and must be maintained at airborne concentrations at or below levels specified by law. XYZ Corporation has put into place an extensive program using duffusive samplers to asure both thermselves and governmental inspectors that the airborne concentrations of solvent vapors are within legal limits. Each day, some 300 diffusive samplers are worn by workers for an eight-hour shift. Then, after being worn, they are placed into small, individual, air-tight glass jars and brought to the company laboratory for analysis. Although the process is largely automated, with the high number of samples taken daily and the occasional changes in plant operations, there is a high probability of errors occuring in the sampling protocol. Because human health is at risk, the possiblity of such errors must be minimized. The following cases illustrate how the present invention can reduce the possibility of errors occuring.

XYZ Corporation has the activated charcoal in the diffusive samplers pretreated with halothane so that, at the time each sampler is placed into use, it will contain a known quantity of halothane. As the sampler is used, halothane diffuses from the sampler. After sampling, the diffusive sampler is opened in the laboratory and the adsorbent placed into a slightly larger volume of carbon dissulfide. It is gently shaken for twenty minutes to establish a controlled desorption period. At the end of this desorption period, a small aliquot of the carbon disulfide is injected into a gas chromatograph for analysis. The peaks that are observed in the resulting chromatogram include those of the solvent vapors as well as a peak from the halothane that still resided on the charcoal after the exposure period. The magnitudes of all peaks, as well as the substances that they represent, are determined electronically as the chromatogram is taken. Halothane is selected as the test agent because, in addition to its being stable and sufficiently volatile to desorb from the sampler, it is not used at this site and, therefore, there are no external concentrations of halothane vapors that could confound the normal losses of halothane from the diffusive sampler.

Case 1 . The amount of halothane found in the samplers from most of the other operations ranges from 40% to 60% of the original amount of solvent placed in the samplers. This loss is consistent with proper use of the samplers in an eight-hour shift. A calibration curve that correlates loss of halothane from the sampler with environmental effects influencing uptake of solvent vapors is used to obtain better estimates of the worker's exposures than would be possible using (as is the current practice) the uptake of solvent of the sampler as the sole reference point for estimating the exposures.

Case 2 . The quantity of halothane in a large number of samplers from one shift is what would be expected in an unused diffusive sampler. On further inquiry it is learned that, to avoid having high levels of solvent vapors found at her site, a foreman had ordered that the samplers not be worn. However, the seals on the samplers glass containers were broken to indicate (falsely) that they had been worn. Disciplinary action is taken and the site is resampled. The high concentrations of vapor found at the site result in additional protective measures taken to reduce workers' exposures.

Case 3. Only 10% of the original halothane is found on one badge. Also, the results for the solvent vapors are very high. Upon additional questioning, it is discovered that this sampler was used in a previous shift, and after being used, was left open at the site for an additional twenty-four hours by mistake instead of being placed in an airtight container and sent back to the laboratory for anaylsis. This accounts for both the high amount of solvent vapors collected by the sampler and the far-above-average loss of halothane from the sampler. The high amount of solvent taken up by the sampler does not in this case, lead to undue alarm; rather, by merely retesting at the site, actual exposures can be confirmed.

It will be apparent to those skilled in the art of diffusive samplers that many modifications and substitutions can be made to the preferred embodiments described herein without departing from the spirit and scope of the present invention, which is defined by the appended claims.

What is claimed is:

1. A diffusive sampler for sampling an analyte in a fluid comprising:
    a sorbent, said sorbent being selected from those adapted to adsorb said analyte from a fluid when exposed to said fluid; and
    sorbate means carried by said sorbent, said sorbate means being desorbable from said sorbent into said fluid when said sampler is exposed to said fluid,
    said sorbate being desorbed from said sorbent and said analyte being sorbed by said sorbent when said sorbent is exposed to said fluid.

2. The diffusive sampler as recited in claim 1, further comprising:
    a housing for containing said sorbent;
    a sorbate- and analyte-permeable membrane carried by said housing with said membrane positioned between said fluid and said sorbent, said membrane spaced apart from said sorbent so as to define a gap.

3. The diffusive sampler as recited in claim 1, wherein said barrier is a fluid- and sorbent-permeable matrix.

4. The diffusive sampler as recited in claim 1, wherein said sorbate means includes a halogenated anesthetic agent.

5. The diffusive sampler as recited in claim 4, wherein said halogenated anesthetic agent is halothane.

6. The diffusive sampler as recited in claim 1, wherein said sorbent is made of activated carbon.

7. The diffusive sampler as recited in claim 1, wherein said sorbate means further comprises:
    a first sorbate having a first desorption rate; and
    a second sorbate having a second desorption rate, said second desorption rate being different from said first desorption rate.

8. The diffusive sampler as recited in claim 7, wherein said first sorbate is a halogenated anesthetic agent and said second sorbate is p-fluorobromobenzene.

9. A diffusive sampler for sampling an analyte in a fluid comprising:
    a housing having an opening;
    a sorbent carried within said housing, said sorbent being selected from those adapted to sorb said analyte from a fluid when exposed to said fluid; and
    sorbate means carried by said sorbent, said sorbate means being desorbable from said sorbent into said fluid when said sampler is exposed to said fluid,
    said sorbate being desorbed from said sorbent and said analyte being sorbed by said sorbent when said fluid enters said sampler through said opening.

10. The diffusive sampler as recited in claim 9, wherein said sorbate means includes a halogenated anesthetic agent.

11. The diffusive sampler as recited in claim 10, wherein said halogenated anesthetic agent is halothane.

12. The diffusive sampler as recited in claim 9, wherein said sorbent is made of activated carbon.

13. The diffusive sampler as recited in claim 9, wherein said sorbate means further comprises:
    a first sorbate having a first desorption rate; and
    a second sorbate having a second desorption rate, said second desorption rate being different from said first desorption rate.

14. The diffusive sampler as recited in claim 13, wherein said first adsorbate is a halogenated anesthetic agent and said second sorbate is p-fluorobromobenzene.

15. The diffusive sampler as recited in claim 14, wherein said halogenated anesthetic agent is halothane.

16. A diffusive sampler for sampling an analyte in a fluid comprising:
    an impermeable housing having an opening;
    a sorbent carried within said housing, said sorbent being selected from those adapted to sorb said analyte from a fluid when exposed to said fluid; and
    a barrier carried by said housing, said sorbent positioned between said barrier and said opening,
    said analyte being sorbed by said sorbent when said fluid enters said sampler through said opening and passes through said barrier to said sorbent.

17. The diffusive sampler as recited in claim 16, wherein said barrier is an analyte-permeable membrane.

18. The diffusive sampler as recited in claim 16, wherein said barrier is an analyte-permeable matrix.

19. The diffusive sampler as recited in claim 17, further comprising:
    a first sorbate carried by said sorbent and having a first desorption rate; and
    a second sorbate carried by said sorbent and having a second desorption rate, said second desorption rate being different from said first desorption rate,
    said first and said second sorbates being desorbed through said barrier when said sampler is exposed to said fluid.

20. The diffusive sampler as recited in claim 18, further comprising:
    a first sorbate carried by said adsorbent and having a first desorption rate; and
    a second sorbate carried by said sorbent and having a second desorption rate, said second desorption rate being different from said first desorption rate,
    said first and said second sorbates being desorbed through said fluid barrier when said sampler is exposed to said fluid.

* * * * *